United States Patent [19]

Galwey et al.

[11] Patent Number: 4,498,039
[45] Date of Patent: Feb. 5, 1985

[54] INSTRUMENT FOR USE WITH AN ELECTROCHEMICAL CELL

[75] Inventors: Ronald K. Galwey, Los Gatos; Kay K. Kanazawa, San Jose, both of Calif.

[73] Assignee: International Business Machines Corporation, Armonk, N.Y.

[21] Appl. No.: 49,525

[22] Filed: Jun. 18, 1979

[51] Int. Cl.$^3$ .............................................. G05F 1/46
[52] U.S. Cl. .................................. 323/234; 204/288; 204/406; 204/412
[58] Field of Search .................... 204/195 F, 228, 406, 204/412, 435; 323/4, 19, 40, 234, 265, 270 273, 280; 330/260

[56] References Cited

U.S. PATENT DOCUMENTS

| | | | |
|---|---|---|---|
| 3,388,317 | 6/1968 | Birman | 323/40 X |
| 3,555,402 | 1/1971 | Bozarth et al. | 323/4 |
| 3,689,848 | 9/1972 | Geffe et al. | 330/260 X |
| 3,855,101 | 12/1974 | Wilson | 204/195 R |
| 4,065,374 | 12/1977 | Asami et al. | 204/228 |
| 4,227,988 | 10/1980 | Galwey et al. | 204/406 |

OTHER PUBLICATIONS

Barclay et al., "Pulse-Potentiostatic Plating", IBM Technical Disclosure Bulletin, vol. 15, No. 7, Dec. 7, 1972, p. 2168.
Greef, "Instruments for Use in Electrode Process Research", Journal of Physics E, Scientific Instruments, vol. 11, 1979, pp. 1-12.
Gabrielle et al., "Compensation de la Chute Ohmique Par Une Methode Analogigue", Journal Electrochimica, vol. 22, 1977, pp. 255-260.
Smith, Modern Operational Circuit Design, John Wiley & Sons, Inc., 1971, pp. 155-159.

Primary Examiner—William H. Beha, Jr.
Assistant Examiner—Jeffrey Starrett
Attorney, Agent, or Firm—Joseph E. Kieninger

[57] ABSTRACT

An improved instrument for use with an electrochemical cell that provides a system having enhanced stability and increased bandwidth. The instrument includes a voltage to current converter which drives the cell. The current output of the voltage to current converter is linearly proportional to the differential voltage input. The voltage to current converter drives the cell in both the potentiostatic mode and in the galvanostatic mode of operation.

3 Claims, 4 Drawing Figures

INSTRUMENT FOR USE WITH AN ELECTROCHEMICAL CELL

TECHNICAL FIELD

This invention relates to an improved instrument for use with electrochemical cells in potentiostatic and galvanostatic studies and, more particularly, to an instrument that includes a voltage to current converter to drive the electrochemical cell.

It is a primary object of this invention to provide an improved instrument for use with an electrochemical cell which provides a large bandwidth.

It is another object of this invention to provide an improved instrument for use with an electrochemical cell which provides a large system bandwidth while maintaining system stability.

It is yet another object of this invention to provide an improved instrument where the configurational changes required for a change from potentiostatic to galvanostatic mode are minimal.

It is a further object of this invention to provide an improved instrument in which the cell current and the cell's reference electrode potential and conveniently monitored.

It is still another object of this invention to provide an improved instrument in which the cell current can be monitored without introducing an additional high current device.

BACKGROUND ART

Electrochemical cells are widely used for electrochemical and biological applications. Typically, as shown in FIG. 1, an electrochemical cell 10 has a working electrode 12, a non-current carrying reference electrode 14 and a counter electrode 16. Controlling and measuring the electrical parameters of an electrode reaction in a cell is done by potential, current and charge control means. The two most common modes of operation are the potential control or potentiostatic mode and the current control or galvanostatic mode. A review article by R. Greef covering this subject matter is published in *Journal of Physics E, Scientific Instruments*, Vol. 11, 1978, pages 1–12 (printed in Great Britain).

Modern potentiostatic control systems for use with electrochemical cells usually use an operational amplifier 18 in a feedback control configuration as shown in FIG. 1. These operational amplifiers are voltage amplifiers whose output voltage, $V_o$, is linearly proportional to the difference between two input voltages ($V_{in} - V_r$). Because of the extremely high voltage gain K of operational amplifiers, $V_o$ is of such a magnitude that the voltage induced in the reference electrode $V_r$ is virtually equal to $V_{in}$. Specifically, the voltage $V_o$ applied across the cell causes a cell current to flow of such magnitude that the corresponding $V_r$ is equal to $V_{in}$. In other words, the voltage source (here the operational amplifier) induces a cell current which is related to $V_r$ and so acts as a source of current in the sense described in U.S. Pat. No. 3,855,101.

This type of potentiostatic control systems exhibit instabilities due to both electrochemical cell impedance, cell current monitoring circuits and the roll off characteristics of the operational amplifier. To improve the stability of these systems they are operated with a restricted bandwidth. These systems also require an additional high current device to measure the current which increases the cost and increases the problems of thermal stability. In addition, changing from a potentiostatic control mode to a galvanostatic mode is difficult and requires several other components.

BRIEF DESCRIPTION OF THE DRAWINGS

In the accompanying drawings forming a material part of this disclosure.

DISCLOSURE OF THE INVENTION

For a further understanding of the invention and of the objects and advantages therefor, reference will be had to the following description and accompanying drawings and to the appended claims in which the various novel features of the invention are more particularly set forth.

BEST MODE FOR CARRYING OUT THE INVENTION

Figure 1:
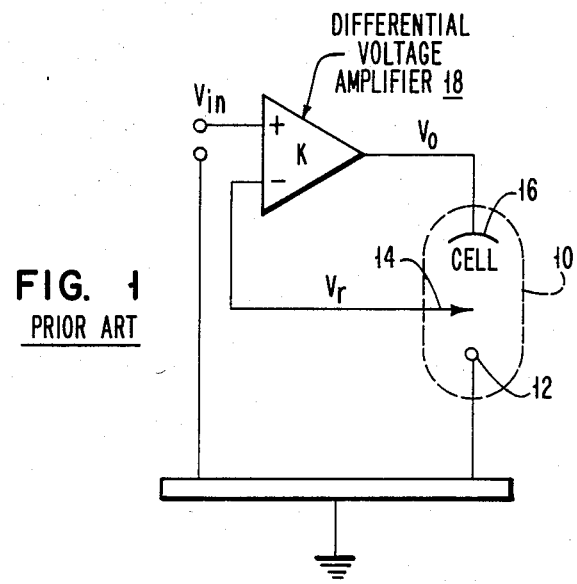
FIG. 1 is a schematic view illustrating the prior art type instrument used with an electrochemical cell.
Figure 2:
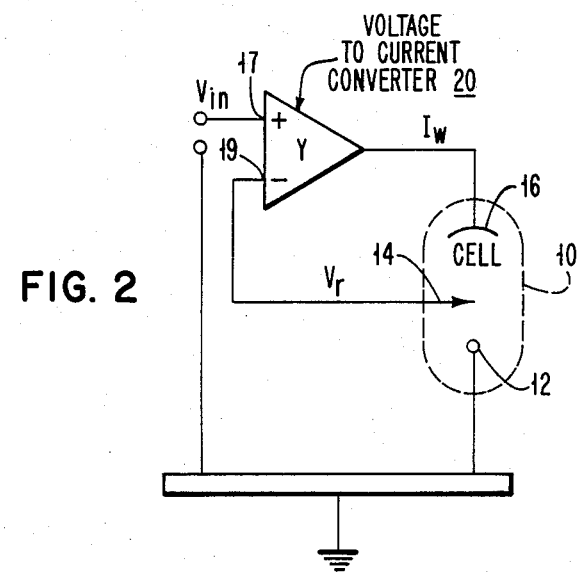
FIG. 2 is a schematic view illustrating an improved instrument operated in the potentiostatic mode in accordance with this invention.

As shown in FIG. 2, the instrument operating in a potentiostatic mode includes a voltage converter 20 in which the output current $I_w$ is linearly proportional to the difference between the voltage $V_{in}$ applied to the non-inverting input 17 and the voltage $V_r$ applied to the inverting input 19. The converter 20 is connected to an electrochemical cell previously described in FIG. 1. The converter 20 is characterized by a forward transfer admittance Y, defined as the ratio of the output current $I_w$ to the input voltage difference $V_{in} - V_r$. Whereas the prior art instruments of the type shown in FIG. 1 have an output voltage $V_o$, which is proportional to $V_{in} - V_r$, the instruments in accordance with this invention have an output current $I_w$, which is proportional to the input voltage difference. The output impedance of the voltage to current converter 20 is much larger than the cell impedance. Use of the voltage to current converter 20 overcomes many of the limitations of prior art electrochemical instrumentation.

Figure 3:
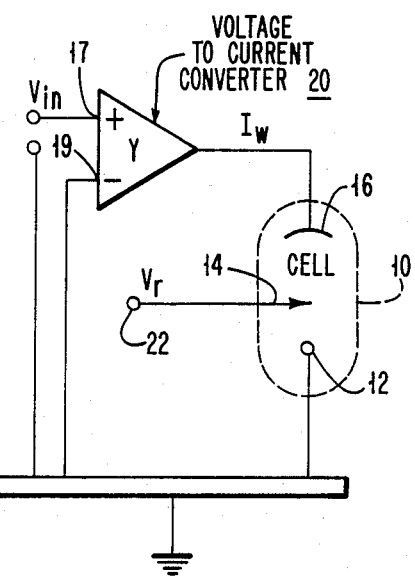
FIG. 3 is a schematic view illustrating an improved instrument operated in the galvanostatic mode in accordance with this invention.

As shown in FIG. 3, the instrument operating in a galvanostatic mode includes an electrochemical cell as described in FIG. 1 and a voltage to current converter 20 in which the output current $I_w$ is linearly proportional to the voltage $V_{in}$ applied to the non-inverting input 17. The converter 20 is characterized by a forward transfer admittance Y, defined as the ratio of the output current $I_w$ to the input voltage $V_{in}$. In this instrument, the potential of the electrochemical reference electrode 14 can be connected to a high impedance voltmeter through terminal 22.

The difference between operating the instrument in a potentiostatic mode as shown in FIG. 2 and in a galvanostatic mode as shown in FIG. 3 is that the inverting input 19 of the converter 20 is connected to the reference electrode in the potentiostatic mode, whereas it is connected to ground in the galvanostatic mode. In the galvanostatic mode the reference electrode is connected to a high impedance voltmeter.

Figure 4:
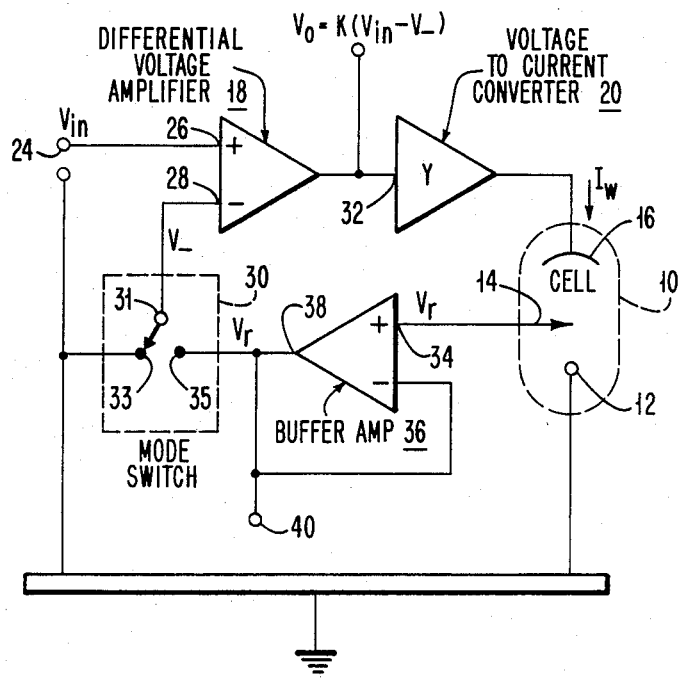
FIG. 4 is a schematic view illustrating a preferred embodiment of an improved instrument in accordance with this invention.

In a preferred embodiment as shown in FIG. 4, the instrument can be operated in either a potentiostatic mode or a galvanostatic mode. The external input voltage 24 is connected to the non-inverting input 26 of the differential amplifier 18. The input voltage 24 is of the order of 0 volts up to ±5 volts and is of the type well known in the industry. For example, the voltage may take the form of DC voltages, ramp voltages, pulse voltages, sinusoidal voltages and the like. The inverting input 28 of the differential amplifier 18 is connected to the mode switch 30. Mode switch 30 may be a manually operated switch, a relay or an electronic switch. In the galvanostatic mode, the mode switch 30 grounds the inverting input 28 by the solid arrow between terminals 31 and 33 shown in FIG. 4 so that the voltage $V_-$ at the inverting input 28 is zero.

The operation of the instrument will first be described assuming a galvanostatic mode. The voltage output $V_o$ of the differential amplifier 18 is proportional to the difference between the input voltages $V_{in}$ and $V_-$. In the galvanostatic mode, since the input voltage $V_-$ is 0, then the output voltage $V_o$ is equal to $KV_{in}$, where K is the voltage gain of the differential amplifier 18. The output voltage $V_o$ is connected to the input 32 of the voltage to current converter 20. The voltage to current converter 20 is characterized by a forward transfer admittance Y. The current $I_w$ from the converter 20 flows into the electrochemical cell 10 and is defined by $I_w = V_o Y$. The current flowing through the cell 10 from the counter electrode 16 to the working electrode 12 induces a voltage $V_r$ in the reference electrode 14. The reference electrode 14 is connected to the input 34 of a non-inverting, unity gain buffer amplifier 36. The output voltage at the output 38 of buffer amplifier 36 has a magnitude $V_r$ and is connected to a terminal 40 for monitoring the reference electrode potential.

The operation of the instrument will next be described assuming a potentiostatic mode. The voltage $V_r$ from the buffer output 38 is still equal to the voltage of the reference electrode 14. In the potentiostatic mode however, the mode switch 30 connects the output 38 of the buffer amplifier 36 to the inverting input 28 of the differential amplifier 18 by connecting terminals 31 and 35 and disconnecting terminals 31 and 33. The input 24 to the non-inverting input 26 of the differential amplifier 18 is still $V_{in}$. Thus, the output of the differential amplifier 18 is $V_o = K(V_{in} - V_r)$. This voltage $V_o$ serves both as an error signal to drive the voltage to current converter 20 and as a voltage by which the cell current can be monitored. This voltage $V_o$, being connected to the input 32 of the voltage to current converter 20 is directly proportional to the cell current. Prior art potentiostats in which the cell is driven by a voltage source and in which the cell current is monitored by a current follower requires high current capabilities from both the voltage source and the current follower. In this instrument, only a single, high current source, that is, the converter 20, is required.

The voltage to current converter 20 can take a variety of forms. There are circuits in which the load (cell) is ungrounded, circuits in which the load is referenced to a virtual ground, and circuits in which the load is grounded. While each of these converter circuits would require modifications in the details of the instrumental circuitry, it would be readily implemented and understood by those skilled in the art.

INDUSTRIAL APPLICABILITY

The advantages of driving the cell using a voltage to current converter in accordance with this invention are that it provides a stable instrument for analyses requiring high frequencies, it lends itself naturally to switching between galvanostatic and potentiostatic modes, and it monitors the cell current without requiring another high current device. This instrument would be particularly useful for applications requiring large bandwidths such as pulse and step polarography, noise measurements and high frequency AC studies.

While the invention has been particularly shown and described with reference to preferred embodiments thereof, it will be understood by those skilled in the art that various changes in the form and details may be made therein without departing from the spirit and scope of the invention.

We claim:

1. An instrument for use with an electrochemical cell having a counter electrode, a reference electrode and a grounded working electrode, said instrument operating in a potentiostatic mode and comprising:
   a voltage to current converter having an inverting input connected to the reference electrode, a non-inverting input and an output, said output connected to the counter electrode, said converter having a current output that is linearly proportional to the difference between the voltages at said non-inverting input and said inverting input.

2. An instrument for use with an electrochemical cell having a counter electrode, a reference electrode and a grounded working electrode, said instrument operating in a potentiostatic mode and comprising:
   a terminal;
   differential amplifier means having an inverting input connected to said terminal, a non-inverting input connected to an external voltage source and an output;
   a voltage to current converter having an input connected to said amplifier means output and an output connected to the counter electrode, said converter having a current output that is linearly proportional to the voltage input; and
   buffer amplifier means having a non-inverting input connected to the reference electrode, an inverting input connected to said terminal and an output connected to said terminal.

3. An instrument for use with an electrochemical cell having a counter electrode, a reference electrode and a grounded working electrode, said instrument operating in either a galvanostatic mode or a potentiostatic mode and comprising:
   a terminal connected to an external voltmeter;
   differential amplifier means having an inverting input, a non-inverting input connected to an external voltage source and an output;
   a voltage to current converter having an input connected to said amplifier means output and an output connected to the counter electrode, said converter having a current output that is linearly proportional to the voltage input;
   buffer amplifier means having a non-inverting input connected to the reference electrode, an inverting input connected to said terminal and an output connected to said terminal; and
   switch means that is connected between said differential amplifier means inverting input, said terminal and ground wherein said inverting input is connected to said terminal when operating in a potentiostatic mode and wherein said inverting input is connected to ground when operating in a galvanostatic mode.

* * * * *